United States Patent [19]
Baker

[11] 3,931,313
[45] Jan. 6, 1976

[54] SCHIFF'S BASE DICHLOROACETAMIDES
[75] Inventor: Don R. Baker, Orinda, Calif.
[73] Assignee: Stauffer Chemical Company, Westport, Conn.
[22] Filed: Nov. 1, 1974
[21] Appl. No.: 519,895

Related U.S. Application Data
[62] Division of Ser. No. 272,271, July 17, 1972, Pat. No. 3,867,444.

[52] U.S. Cl. .................... 260/561 H; 260/561 HL
[51] Int. Cl.² ...................................... C07C 103/34
[58] Field of Search ................. 260/561 H, 561 HL

[56] References Cited
FOREIGN PATENTS OR APPLICATIONS
1,167,849  4/1964  Germany .................. 260/561 H
2,133,793  12/1972  France

*Primary Examiner*—C. Davis
*Attorney, Agent, or Firm*—Harry A. Pacini

[57] ABSTRACT

Schiff's base dichloroacetamides having the formula

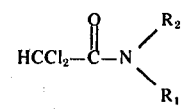

in which $R_1$ is selected from the group consisting of alkenyl, alkyl, alkynyl and alkoxyalkyl; and $R_2$ is selected from the group consisting of alkenyl-1, lower alkylimino, cyclohexenyl-1 and lower alkyl substituted cyclohexenyl-1. The compounds of this invention are useful as herbicidal antidotes.

3 Claims, No Drawings

SCHIFF'S BASE DICHLOROACETAMIDES

This is a division of application Ser. No. 272,271, filed July 17, 1972, now U.S. Pat. No. 3,867,444.

DESCRIPTION OF THE INVENTION

This invention relates to certain novel Schiff's base dichloroacetamides which are useful as herbicidal antidotes. The compounds of the present invention are new compositions of matter and correspond to the general formula

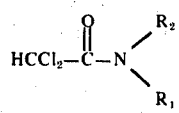

in which $R_1$ is selected from the group consisting of alkyl having from 1 to 6 carbon atoms, inclusive, alkenyl having from 3 to 6 carbon atoms, inclusive, alkynyl having from 3 to 6 carbon atoms, inclusive, and alkoxyalkyl having a total of from 2 to 8 carbon atoms, inclusive; and $R_2$ is selected from the group consisting of alkenyl-1 having from 3 to 6 carbon atoms, inclusive, alkylimino having from 1 to 6 carbon atoms, inclusive, cyclohexenyl-1, and lower alkyl substituted cyclohexenyl-1 wherein said lower alkyl has from 1 to 4 carbon atoms, inclusive.

In the above description, the following preferred embodiments are intended for the various substituent groups: alkyl preferably includes those members having from 1 to 6 carbon atoms in both straight chain and branched chain configurations, for example, methyl, ethyl, n-propyl, isopropyl, n-butyl, sec.-butyl, 1,1-dimethylbutyl, n-hexyl and the like; alkenyl preferably includes those members in both straight chain and branched chain configurations having at least one double bond and from 3 to 6 carbon atoms, inclusive; alkynyl preferably includes those members in both straight chain and branched chain configurations having at least one triple bond and from 3 to 6 carbon atoms, inclusive; lower alkyl preferably includes those members having from 1 to 4 carbon atoms, inclusive, in both straight chain and branched chain configurations for example, methyl, ethyl, n-propyl, isopropyl, n-butyl, sec.-butyl and the like.

The compounds of the present invention are prepared by several different methods, depending upon the nature of the starting materials and the products desired. The non-hydrazide compositions are prepared by the displacement and rearrangement reaction between an appropriate Schiff's base and an acid chloride, dichloroacetyl chloride. The Schiff's base is the product of a primary amine with a carbonyl-containing compound, such as ketone or aldehyde. The hydrazide-containing compositions are prepared by the reaction between an acid chloride, dichloroacetyl chloride and an alkyl hydrazone. The reactions proceed readily in the liquid phase. The employment of a solvent is useful, although unnecessary. Such solvents as diethyl ether and the like, facilitate processing of the reaction product. The reactions are carried out at temperatures which permit operation in the liquid phase. The preferable temperatures are between about room temperature and reflux temperature of the solvent, if a solvent is employed. In each instance after the reaction is complete, the recovery of the product is carried out by normal work-up procedures such as crystallization, sublimation or distillation.

The compounds of the present invention and their preparation are more particularly illustrated by the following examples. Following the examples is a table of compounds which are prepared according to the procedures described herein.

EXAMPLE I

Preparation of N-allyl N-(1-hexenyl)-dichloroacetamide.

Preparation of Intermediate: N-cyclohexylidene allyl-amine. Cyclohexanone (52 ml.) was added over a period of about 20 minutes to a stirred and cooled solution of allylamine (38 ml., 0.50 mole) in 100 ml. diethyl ether. The reaction mixture was stirred for about 20 minutes at room temperature. Potassium hydroxide pellets (17 g.) were added to the mixture and then heated to reflux (45°C.) with stirring for about 30 minutes. The resulting layers were separated and the organic layer was dried over sodium carbonate. The organic solvent was evaporated in vacuo. There was obtained 55 g. of the intermediate, an oil.

Dichloroacetyl chloride (4.8 ml., 0.05 mole) was added to a solution of N-cyclohexylidene allylamine (0.6 g.) in 100 ml. of diethyl ether and 7.0 ml. triethylamine. During the addition, the reaction mixture was cooled. After standing for about 16 to 18 hours, the reaction mixture was washed with two 100 ml. portions of water. Magnesium sulfate was added during the last wash to aid phase separation. The resulting organic solution was dried over magnesium sulfate. Upon evaporation in vacuo of the organic solvent, there was obtained 12.4 g. of the title compound, an oil, $n_D^{30} = 1.5093$.

EXAMPLE II

Preparation of N-t-butyl N-(1-butenyl)-dichloroacetamide.

In a similar procedure as Example I, 6.6 g. (0.052 mole) N-butylidene-t-butylamine was reacted with 4.8 ml. (0.05 mole) dichloroacetyl chloride in 100 ml. diethyl ether and 7.2 ml. triethylamine. There was obtained 9.3 g. of the title compound, an oil, $n_D^{30} = 1.4858$.

EXAMPLE III

Preparation of N-ethyl N-(3-pent-3-enyl)-dichloroacetamide.

In a similar procedure as Example I, 5.9 g. (0.052 mole) N-3-pentylidene ethylamine was reacted with 4.8 ml. (0.05 mole) dichloroacetyl chloride in 100 ml. diethyl ether and 7.2 ml. triethylamine. There was obtained 7.7 g. of the title compound, an oil, $n_D^{30} = 1.4826$.

EXAMPLE IV

Preparation of Acetone N-methyl dichloroacethydrazide.

Preparation of Intermediate: Acetone N-methyl hydrazide. Acetone (72 ml.) was added to a stirred and cooled solution of methyl hydrazine (46 g., 1.00 mole) in 100 ml. benzene and 1 ml. glacial acetic acid. After the addition was complete, the solution was heated to reflux and 21 ml. of aqueous solution was removed as benzene-water azeotripe. The reaction solution was cooled and filtered through a bed of sodium carbonate and concentrated by removal of solvent in vacuo. There was obtained a yield of 80 g. of the title intermediate, an oil. The structure was confirmed by nuclear magnetic resonance, which also indicated about 21 mole per cent benzene also present.

To prepare the title compound, 4.8 ml. (0.05 mole) dichloroacetyl chloride was added to a solution of acetone N-methyl hydrazide (5.5 g., 0.05 mole) in 100 ml. diethyl ether and 7.2 ml. triethylamine. The reaction mixture was stirred and cooled during the addition. After standing for about one hour the reaction mixture was washed with two 100 ml. portions of water and dried over magnesium sulfate. The solvent was evaporated in vacuo to yield 5.0 g. of the title compound, an oil, $n_D^{30} = 1.5046$.

Other compounds were prepared in analogous reactions employing the appropriate starting materials as outlined above. The following is a table of Compounds representative of those embodied by the present invention. Compound numbers have been assigned to them and are used for identification throughout the balance of the specification.

ber of weed pests, both broadleaf and grasses, at different concentrations varying with the resistance of the weeds to be controlled. Some examples of these compounds are described and claimed in U.S. Pat. Nos. 2,913,327, 3,037,853, 3,175,897, 3,185,720 and 3,198,786.

It has been found in practice that the use of the thiocarbamate-type herbicides, when employed as an herbicide in corn fields, sometimes causes serious injury to the corn plants. Various unfavorable effects can be noted. For example, when used in the recommended amounts in the soil to control many broadleaf and grass weeds, serious malformation and stunting of the corn plants result. This abnormal growth in the corn plants is undesirable and results in loss of crop yield.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbi-

TABLE I $$\text{HCCl}_2-\overset{\overset{\displaystyle O}{\|}}{C}-N\overset{R_2}{\underset{R_1}{\diagdown}}$$

| Compound Number | $R_1$ | $R_2$ | $n_D^{30}$ |
|---|---|---|---|
| 1 | $CH_2CH=CH_2$ |  | 1.5093 |
| 2 | $C(CH_3)_3$ | $-CH=CHCH_2CH_3$ | 1.4858 |
| 3 | $C(CH_3)_2C\equiv CH$ | $-CH=CHCH_2CH_3$ | semi-solid |
| 4 | $C_2H_5$ | $-C(C_2H_5)=CHCH_3$ | 1.4826 |
| 5 | $CH_2CH_2CH_2CH_3$ | $-CH=CHCH_2CH_3$ | 1.4930 |
| 6 | $CH_2CH_2CH_3$ |  | 1.5152 |
| 7 | $CH_2CH_2CH_3$ | $-C(CH_3)=CHCH_2CH_3$ | 1.5046 |
| 8 | $CH_3$ | $-N=C(CH_3)_2$ | 1.5046 |
| 9 | $CH_2CH_2OCH_3$ | 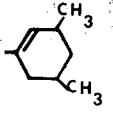 | 1.4620 |
| 10 | $CH_2CH_2CH_2OCH(CH_3)_2$ | 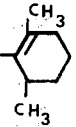 | 1.5000 |

The compounds of this invention have been found to be active as effective protectants or antidotes against injury by thiocarbamate herbicides to various beneficial plants, especially corn.

Among the many herbicidal compounds commercially available, the thiocarbamate herbicides alone or mixed with other herbicides such as triazines have reached a relatively high degree of commercial success. These herbicides are immediately toxic to a large numcidal compound or combination to control undesirable plant species readily may be made. Within the present invention the prevention of injury to a desired crop species in the presence of a specific compound or combination may be achieved. The beneficial plant species which can be protected by this method is not intended to be limited by the specific crops employed in the examples.

The herbicidal compounds employed in the method of this invention are active herbicides of a general type. That is, the members of the classes are herbicidally effective against a wide range of plant species with no discrimination between desirable and undesirable species. The method of controlling vegetation comprises applying an herbicidally effective amount of the herein described herbicidal compounds to the area or plant locus where control is desired.

An herbicide is used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants", it is meant germinant seeds, emerging seedlings, and established vegetation, including the roots and above-ground portions.

The herbicidal active compositions and utility of this invention comprising thiocarbamates in combination with antidote compounds described hereinabove were tested in the following manner.

Corn Seed Treatment

Flats were filed with Felton loamy sand soil. Soil incorporated herbicides were applied at this time. The soil from each flat was placed into a five-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contains 7 mg. of herbicide which equals one pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six PAG 344T field corn seeds were planted in each row. Rows were approximately 1½ inches apart in the flat. Seeds were treated by placing 50 mg. of the antidote compound with 10 grams of corn seed in a suitable container and shaking them until the seeds were uniformly covered with the compound. Antidote compounds also were applied as liquid slurries and powders or dusts. In some cases, acetone was used to dissolve powdered or solid compounds so they could be more effectively applied to the seeds.

After the flats were seeded, they were covered wtih the one pint of soil which had been removed just prior to planting. Flats were placed on greenhouse benches where temperatures ranged from 70°-90°C. Flats were watered by sprinkling as needed to assure good plant growth. Per cent control ratings were taken two to four weeks after the treatments were applied.

In each test, the herbicide was applied alone, in combination with the seed protectant, and the seed protectant is applied alone to check for phytotoxicity. Untreated seeds were planted in adjacent rows to test for lateral displacement through the soil of the candidate compounds and possible beneficial effect. The degree of the effect was noted by compraison with the control. The results of these tests are tabulated in Table II.

TABLE II

| COM- POUND NUMBER | EPTC lb/A | Seed Treatment % w/w | Per Cent Injury to Corn from EPTC* Treated Seed | Per Cent Injury (4 wks) Untreated Seed |
|---|---|---|---|---|
| 1 | 6 | 0.5 | 0 | 60$^{MF}$ |
| 2 | 6 | 0.5 | 30$_{MF}^{ST}$ | 70** |
| 3 | 6 | 0.5 | 10$^{ST}$ | 60 |
| 4 | 6 | 0.5 | 10$^{ST}$ | 65 |
| 5 | 6 | 0.5 | 0 | 45 |
| 6 | 6 | 0.5 | 10 | 65 |
| 7 | 6 | 0.5 | 30 | 75** |
| 8 | 6 | 0.5 | 0 | 45 |
| 9 | 6 | 0.5 | 70 | 80 |
| Control: | 6 | — | — | 80 |

MF = Malformation
ST = Stunting
*EPTC = S-ethyl-dipropylthiocarbamate
10 ** = Rating - 2 weeks

Multicrop Antidote Incorporation Screen

Plastic flats measuring 6 × 9.5 × 3 inches were filled with 7 lb. of Felton loamy sand soil. EPTC was incorporated at 5 lb/A, while a constant rate of 5 lb/A of the additive was used. EPTC and the herbicide additive were applied separately by pipetting measured amounts of the appropriate stock solutions into the soil during incorporation in a 5 gallon rotary cement mixer. Stock solution for EPTC was prepared as follows: 6700 mg. of EPTC 6E (75.5%) was diluted with 500 ml. of deionized water so that 2 ml. equals 5 lb/A/plastic flat.

Additive stock solutions were prepared by diluting 102 mg. of technical material with 10 ml. of acetone 1% Tween 20 so that 2 ml. equals 5 lb/A/plastic flat.

After the soil was treated with both herbicide and additive the soil was transferred from the mixer back into the plastic flat where it was then prepared for seeding. The initial step in preparation was to remove a one pint sample of soil from each flat to be retained and used to cover the seeds after planting. The soil was then leveled and rows one-quarter inch deep were made in each flat. Flats treated with 5 lb/A of EPTC were seeded to DeKalb XL-44 corn (*Zea maize*), US H9 sugarbeets (*Beta vulgare*), small seeded gray striped sunflower (*Helianthus annus*), Acala cotton (*Gossypium hirsutum*), Brag soybeans (*Glycine max*) and oilseed rape (*Brassica napus*). Seeds were then covered with the pint soil sample removed prior to seeding. The flats were then placed on greenhouse benches where temperatures were maintained between 70°-90°F. The soil was watered by sprinkling to assure good plant growth.

Injury ratings were taken 2 and 4 weeks after the treatments were applied. Soil treated with EPTC alone at ½ or 5 lb/A was included to provide a basis for determining the amount of injury reduction provided by the herbicide antidotes.

With Compound No. 10, after 2 weeks a difference in the amount of injury was observed with the sunflower plants. Whereas all other crops exhibited substantially the same amount of injury as those planted in EPTC treated soil, the sunflower plants in this test were substantially uninjured. After 4 weeks, the sunflower plants remained normal. After 4 weeks, the corn plants were able to recover such that only about 60% injury was observed. The remaining crops at 4 weeks continued to show substantially identical injury as plants in the EPTC treated flats.

The antidote compounds of the present invention can be used in any convenient form. Thus, the antidote compounds can be made into emulsifiable liquids, emulsifiable concentrates, liquid, wettable powder, powders, granular or any other convenient form. In its preferred form, the antidote compounds are admixed with the thiocarbamates and incorporated into the soil prior to or after planting the seed. It is to be understood, however, that the thiocarbamate herbicide can be incorporated into the soil and thereafter the antidote compound can be incorporated into the soil. Moreover, the seed can be treated with the antidote compound and planted into the soil which has been treated with herbicides or untreated with the herbicide and subsequently treated with the herbicide. The addition of the antidote compound does not affect the herbicidal activity of the carbamate compounds.

The amount of the antidote composition present can range between about 0.01 to about 15 parts by weight per each part by weight of thiocarbamate herbicide. The exact amount of antidote compound will usually be determined on economic ratios for the most effective amount usable.

What is claimed is:

1. A compound having the formula

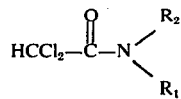

in which $R_1$ is selected from the group consisting of alkyl having from 1 to 6 carbon atoms, inclusive, alkenyl having from 3 to 6 carbon atoms, inclusive, alkynyl having from 3 to 6 carbon stoms, inclusive, and alkoxyalkyl having a total of from 2 to 8 carbon atoms, inclusive; and $R_2$ is alkylimino having from 1 to 6 carbon atoms, inclusive.

2. A compound according to claim 1 in which $R_1$ is alkyl and $R_2$ is alkylimino.

3. A compound according to claim 2 in which $R_1$ is methyl and $R_2$ is 2-isopropylimino.

* * * * *